United States Patent [19]

Rooney et al.

[11] 4,054,652
[45] Oct. 18, 1977

[54] DIHYDRO- AND TETRAHYDRO-IMINOTHIAZINES

[75] Inventors: Clarence S. Rooney, Beaconsfield; Joshua Rokach, Chomedey, both of Canada; Edward J. Cragoe, Jr., Lansdale, Pa.

[73] Assignee: Merck & Co., Inc., Rahway, N.J.

[21] Appl. No.: 696,448

[22] Filed: June 15, 1976

[51] Int. Cl.² .................. C07D 279/06; C07D 279/12; A61K 31/54
[52] U.S. Cl. ...................................... 424/246; 544/53; 544/59; 544/56
[58] Field of Search ...................... 260/243 B, 243 R; 424/246

[56] References Cited

U.S. PATENT DOCUMENTS 3,492,298   1/1970   Rasmussen .................. 260/243 R

OTHER PUBLICATIONS

Zimmermann, Chem. Abstracts, vol. 60, entry 519(b), (1964).
Willems et al., Chem. Abstracts, vol. 54, entry 22657(b), (1960).
Schoberl et al. (I), Liebigs, Ann. der Chemie, vol. 742, pp. 75-84.
Schoberl et al. (II), Liebigs, Ann. der Chemie, vol. 742, pp. 85-95.

Primary Examiner—John M. Ford
Attorney, Agent, or Firm—Harry E. Westlake, Jr.; William H. Nicholson

[57] ABSTRACT

Dihydro- and tetrahydro-iminothiazines are inhibitors of indoleamine-N-methyl transferase in vivo.

5 Claims, No Drawings

DIHYDRO- AND TETRAHYDRO-IMINOTHIAZINES

BACKGROUND OF THE INVENTION

This invention is concerned with the derivatives of dihydro- and tetrahydro-iminothiazines which by virtue of their ability to inhibit indoleamine-N-methyl transferase are useful in the treatment of certain mental aberrations in man, such as schizophrenia.

This invention also relates to processes for the preparation of the imines of this invention; to pharmaceutical compositions comprising the imines; and to a method of treating mental aberrations, such as schizophrenia, comprising the administration of the imines and compositions thereof. The imines may be depicted by the generic structure:

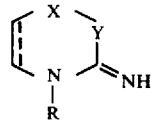

wherein X—Y is —CH$_2$—S— or —S—CH$_2$—.

N,N-dimethylindoleamines such as dimethylserotonin and dimethyltryptamine are psychotomimetic agents and are believed to be produced in excessive amounts by individuals with certain mental aberrations, most commonly classified as schizophrenia. Indoleamine-N-methyl transferase is an enzyme which catalyzes methylation steps in the biosynthesis of these compounds. Accordingly, it is believed by those skilled in the art that inhibitors of this enzyme will be of therapeutic value in management of the body chemistry of patients having mental aberrations such as schizophrenia and thus result in alleviating some of the symptoms of the disease. Thus it is an object of the present invention to provide the above-described imines and their pharmaceutically acceptable acid addition salts; to provide processes for the preparation of such compounds; pharmaceutical compositions comprising such compounds; and to provide methods of treatment comprising administering such compounds and compositions, when indicated for the treatment/management of mental aberrations such as schizophrenia.

DETAILED DESCRIPTION OF THE INVENTION

The novel compounds of this invention have structural formula I:

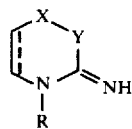

or pharmaceutically acceptable salt thereof, wherein the dotted line represents saturation or unsaturation,
X—Y represents —CH$_2$—S— or —S—CH$_2$; and
R represents C$_{1-2}$ alkyl, especially methyl; with the proviso that when X—Y represents —CH$_2$—S— in a saturated ring, R is methyl.

One embodiment of the novel compounds of this invention is that with structural formula:

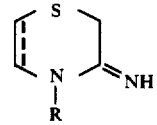

or pharmaceutically acceptable salt thereof.

The pharmaceutically acceptable salts of this invention are acid addition salts prepared from mineral or organic acids commonly employed in the pharmaceutical art, such as hydrobromic, hydrochloric, fumaric, ethane disulfonic, or the like.

The compound, 3-ethyl-2-imino-tetrahydro-1,3-thiazine, excluded from the novel compounds is known in Annalen, 742, 74 (1970). It is, however, active in the novel method of treatment of this invention and forms a part thereof, and is included in the novel pharmaceutical formulations of this invention.

Thus, the novel method of treatment and pharmaceutical compositions of this invention employ compounds of structural formula:

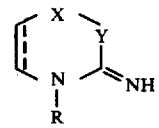

or pharmaceutically acceptable salts thereof, wherein the dotted line represents saturation or unsaturation; X—Y represents —CH$_2$— or —S—CH$_2$—; and R represents C$_{1-2}$ alkyl.

In the novel method of treatment of this invention the route of administration can be oral, rectal, intravenous, intramuscular, or intraperitoneal. Doses of 0.10 to 100 mg./kg./day and preferably of 1 to 10 mg./kg./day of active ingredient are generally adequate, and it is preferred that it be administered in divided doses given two to four times daily.

It is to be noted that the precise unit dosage form and dosage level depend upon the case history of the individual being treated and, consequently, are left to the discretion of a skilled therapist.

Pharmaceutical compositions comprising a compound useful in the novel method of treatment as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and intraperitoneal use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 mg. to 500 mg.

The compounds of this invention are prepared by the following processes:

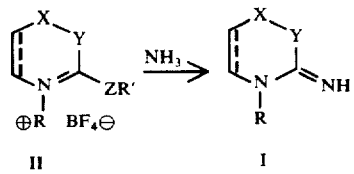

wherein the dotted line represents unsaturation or saturation;

R is C$_{1-2}$ alkyl;
R' is C$_{1-3}$ alkyl;
X—Y is —CH$_2$—S— or —S—CH$_2$—; and
Z is O or S.

The compound of Formula II in a lower alkanol, preferably ethanol at −10 to about 50° C., is treated with ammonia or ammonium hydroxide followed by isolation of the product of Formula I.

Alternatively, especially for the preparation of 2,3-dihydro-2-imino-3-R-6H-1,3-thiazine, the following synthesis may be employed:

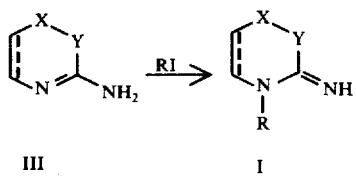

wherein the symbols have the meanings assigned above. This process comprises refluxing for 2–6 hours a compound of Formula I with a reagent of Formula RI with or without a solvent such as a lower alkanol, especially isopropanol.

The starting materials for the novel processes of this invention and processes for preparing them are fully described in the examples that follow.

EXAMPLE 1

2-Imino-3-methyl-tetrahydro-1,3-thiazine Hydrobromide

A solution of 0.945 g. of 5,6-dihydro-2-methyl-thio-4H-1,3-thiazine was dissolved in 10 ml. of methylene chloride at room temperature and 0.460 g. of trimethyloxonium fluoroborate was added. After two hours the methylene chloride was evaporated to dryness and the residue of methyl-5,6-dihydro-2-methylthio-4H-1,3-thiazinium fluoroborate was dissolved in ethanol. Ammonia was bubbled into the solution for ½ hour, the ethanol was evaporated to dryness, and the residue was partitioned between chloroform and aqueous sodium hydroxide solution. The chloroform phase was evaporated to dryness, and the residue was dissolved in isopropanol and the solution was acidified with aqueous hydrobromic acid. Ether was added to incipient cloudiness, and the mixture was stored in the freezer until precipitation was complete. The solids were collected and dried to give 0.740 g. of 2-imino-3-methyltetrahydro-1,3-thiazine hydrobromide, m.p. 168°–171° C.

Employing the procedure substantially as described in Example 1, but substituting for the trimethyloxonium fluoroborate used therein, an equimolecular amount of triethyloxonium fluoroborate, there is produced the intermediate ethyl 5,6-dihydro-2-methylthio-4H-1,3-thiazinium fluoroborate and 3-ethyl-2-imino-tetrahydro-1,3-thiazine hydrobromide, m.p. 194°–195° C.

EXAMPLE 2

3-Imino-4-methyl-tetrahydro-1,4-thiazine Fumarate

A mixture of 5 g. of trimethyloxonium fluoroborate and 5 g. of 3-ethoxy-5,6-dihydro-2H-1,4-thiazine in 75 ml. of methylene chloride was stirred at room temperature for 3 hours after slight warming to cause solution. The solvent was evaporated and the residue of methyl 3-ethoxy-5,6-dihydro-2H-1,4-thiazinium fluoroborate was treated with 50 ml. of concentrated ammonium hydroxide and evaporated to a heavy oil. The oil was dissolved in 50 ml. of 0.5 M hydrochloric acid, washed well with chloroform and made strongly basic with sodium carbonate and then 20% sodium hydroxide solution. The mixture was thoroughly extracted with chloroform and the combined extracts were evaporated to 1.5 g. of oil. The oil (1.2 g.) was dissolved in isopropanol and treated with 1.1 g. of fumaric acid to give 1.1 g. of crystalline 3-imino-4-methyl-tetrahydro-1,4-thiazine fumarate, m.p. 111°–113° C.

Employing the procedure of Example 2, but substituting for the trimethyloxonium fluoroborate used therein an equimolecular amount of triethyloxonium fluoroborate, there is produced the intermediate ethyl 3-ethoxy-5,6-dihydro-2H-1,4-thiazinium fluoroborate and 4-ethyl-3-imino-tetrahydro-1,4-thiazine fumarate.

EXAMPLE 3

2,3-Dihydro 3-imino-4-methyl-2H-1,4-thiazine Hydrochloride

Step A: Preparation of N-methyl thioglycolic acid amide

Methylamine was bubbled through 30 ml. of methyl thioglycolate for 2.5 hours while controlling the temperature at or below room temperature. Volatiles were removed under high vacuum to yield oily N-methyl thioglycolic acid amide.

Step B: Preparation of N-methyl 5,5-diethoxy-3-thiapentanoic acid amide

A mixture of 9.4 g. of bromodiethylacetal, 5 g. of N-methyl thioglycolic acid amide, 1.9 g. of sodium hydroxide, 100 mg. of potassium iodide and 50 ml. of methanol was refluxed 12 hours. The mixture was evaporated to an oil and the residue was largely dissolved in chloroform and filtered. The filtrate was concentrated to dryness, and the residue was chromatographed on silica gel by elution with ethyl acetate. The appropriate fractions were combined and concentrated to dryness to give 6 g. of oily N-methyl 5,5-diethoxy-3-thia-pentanoic acid amide.

Step C: Preparation of 2,3-dihydro 4-methyl-3-oxo-2H-1,4-thiazine

The product from Step B was distilled at 88°–100° C. and 3 mm of mercury pressure over a few drops of 85% phosphoric acid to give 2.6 g. of 2,3-dihydro 4-methyl-3-oxo-2H-1,4-thiazine.

Step D: Preparation of 2,3-dihydro-4-methyl-3-thio-2H-1,4-thiazine

A mixture of 1 g. of 2,3-dihydro-4-methyl-3-oxo-2H-1,4-thiazine, 0.8 g. of phosphorus pentasulfide, and 15 ml. of tetrahydrofuran was refuxed 10 minutes. An additional 0.2 g. of phosphorus pentasulfide was added and refluxing was continued for 1 hour. The mixture was cooled and filtered and the filter cake was washed well with tetrahydrofuran. The combined filtrate and washings were evaporated to an oil. The oil was extracted well with hot benzene and benzene soluble material was chromatographed on silica gel by elution with benzene to give 0.945 g. of 2,3-dihydro-4-methyl-3-thio-2H-1,4-thiazine.

Step E: Preparation of 2,3-dihydro 3-imino-4-methyl-2H-1,4-thiazine hydrochloride A mixture of 0.8 g. of thiazine-thione from Step D, 0.82 g. of trimethyloxonium fluoroborate and 5 ml. of methylene chloride was stirred at room temperature for 30 minutes. The solvent was evaporated and the residue of methyl 3-methylthio-2H-thiazinium fluoroborate was suspended in 10 ml. of ethanol and ammonia was bubbled into the solution for several minutes. The mixture was evaporated to dryness, and the residue was dissolved in 10% acetic acid, washed with 3 volumes of chloroform and made strongly basic with 20% sodium hydroxide solution. The basic solution was extracted with 3 volumes of chloroform which were combined, dried and evaporated to 560 mg. of oil. The residue was dissolved in ether and treated with gaseous hydrogen chloride. The precipitate was collected, washed with ether, and dried to give 500 mg. of 2,3-dihydro 3-imino-4-methyl-2H-1,4-thiazine hydrochloride, m.p. 235° C. (dec.) after darkening at 180° C.

Employing the procedure of Example 3, but substituting for the methylamine used in Step A thereof, an equimolecular amount of ethylamine, followed by Steps B through E, there is produced 2,3-dihydro-4-ethyl-3-imino-2H-1,4-thiazine hydrochloride.

EXAMPLE 4

2,3-Dihydro-2-imino-3-methyl-6H-1,3-thiazine Hydrochloride

Step A: Preparation of 2-amino-4,5-dihydro-4-ethoxy-6H-1,3-thiazine

A mixture of 10 g. of thiourea, 50 ml. of β-chloropropionaldehyde diethyl acetal, 75 ml. of absolute ethanol, and 2 g. of potassium iodide was refluxed for 2 days. The solvent was evaporated, and the residue was partitioned between water and ether. The aqueous phase was extracted twice more with ether, basified with sodium carbonate and extracted 4 times with chloroform. The chloroform was concentrated to dryness, and the residue was thoroughly extracted with ether. The ether extracts were evaporated to a small volume which deposited 6.88 g. of crystalline 2-amino-4,5-dihydro-4-ethoxy-6H-1,3-thiazine.

Step B: Preparation of 2-amino-6H-1,3-thiazine

Ethoxythiazine from Step A (6.38 g.) was treated with polyphosphoric acid (prepared from 50 g. of $P_2O_5$ and 40 ml. of 85% $H_3PO_4$) at 80°–90° for 15 minutes. After cooling, the mixture was treated with ice and water, basified with sodium hydroxide solution and extracted with chloroform. Evaporation of solvent gave 3.6 g. of oily 2-amino-6H-1,3-thiazine.

Step C: Preparation of 2,3-dihydro-2-imino-3-methyl-6H-1,3-thiazine hydrochloride A mixture of the aminothiazine from Step B (1.7g.) and 5 g. of methyliodide and 40 ml. of isopropanol was refluxed 4 hours and then let stand overnight. The solvent was evaporated and the residue was partitioned between water and chloroform. The aqueous phase was washed twice with chloroform, made basic with aqueous sodium hydroxide solution and extracted with chloroform. Evaporation of the chloroform gave 1.15 g. of oil. The oil was dissolved in isopropanol and made acid with concentrated hydrochloric acid. Addition of ether caused precipitation of 2,3-dihydro-2-imino-3-methyl-6H-1,3-thiazine hydrochloride, m.p. 133°–136° C.

Employing the procedure substantially as described in Example 4, Step C, but substituting for the methyl iodide used therein an equimolar amount of ethyl iodide, there is produced 2,3-dihydro-3-ethyl-2-imino-6H-1,3-thiazine hydrochloride.

EXAMPLE 5

Pharmaceutical Compositions

A typical tablet containing 5 mg. of 2-imino-3-methyl tetrahydro-1,3-thiazine hydrobromide per tablet is prepared by mixing together with the active ingredient calcium phosphate, lactose and starch in the amounts shown in the tables below. After these ingredients are thoroughly mixed, the dry mixture is blended for an additional three minutes. This mixture is then compressed into tablets weighing approximately 129 mg. each. Similarly prepared are tablets containing 3-ethyl-2-imino-tetrahydro-1,3-thiazine hydrobromide, 3-imino-4-methyl-tetrahydro-1,4-thiazine fumarate, 4-ethyl-3-imino-tetrahydro-1,4-thiazine fumarate, 2,3-dihydro-3-imino-4-methyl-2H-1,4-thiazine hydrochloride, 2,3-dihydro-4-ethyl-3-imino-2H-1,4-thiazine hydrochloride, 2,3-dihydro-2-imino-3-methyl-6H-1,3-thiazine hydrochloride, and 2,3-dihydro-3-ethyl-2-imino-6H-1,3-thiazine hydrochloride.

Tablet Formula

| Ingredient | Mg. per tablet |
| --- | --- |
| Active Ingredient | 20 mg. |
| Calcium phosphate | 52 mg. |
| Lactose | 45 mg. |
| Starch | 10 mg. |
| Magnesium stearate | 1 mg. |

What is claimed is:

1. A compound of structural formula:

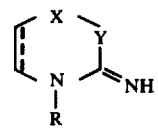

or pharmaceutically acceptable salt thereof, wherein the dotted line is unsaturation or saturation;

X—Y is —CH$_2$—S— or —S—CH$_2$—; and

R is C$_{1-2}$ alkyl, with the proviso that if X—Y represents —CH$_2$—S— in a saturated ring, then R is methyl.

2. The compound of claim 1, with structural formula:

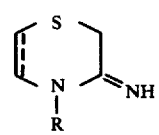

or pharmaceutically acceptable salt thereof, wherein the dotted line is saturation or unsaturation and R is C$_{1-2}$ alkyl.

3. A method of inhibiting indoleamine-N-methyl transferase which comprises the administration to a patient in need of such treatment an effective amount of a compound of formula:

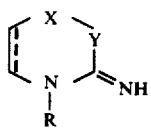

or pharmaceutically acceptable salt thereof, wherein the dotted line is saturation or unsaturation;

X—Y is —CH$_2$—S— or —S—CH$_2$—; and

R is C$_{1-2}$ alkyl.

4. A pharmaceutical composition in unit dosage form comprising a pharmaceutical carrier and an effective amount of a compound of formula:

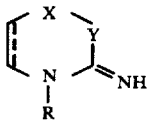

or pharmaceutically acceptable salt thereof, wherein the dotted line is saturation or unsaturation;

X—Y is —CH$_2$—S— or —S—CH$_2$—; and

R is C$_{1-2}$ alkyl.

5. A process for the preparation of a compound of formula:

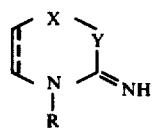

or pharmaceutically acceptable salt thereof, wherein the dotted line is unsaturation or saturation;

X—Y is —CH$_2$—S— or —S—CH$_2$—; and

R is C$_{1-2}$ alkyl, with the proviso that if X—Y represents —CH$_2$—S— in a saturated ring, then R is methyl, characterized in that a compound of formula:

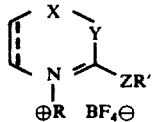

is treated with ammonia or ammonium hydroxide, wherein the dotted line, R and X—Y are as defined above, R' is C$_{1-3}$ alkyl and Z is O or S, with the proviso that if X—Y represents —CH$_2$—S— and the dotted line is saturation, then R is methyl.

* * * * *